United States Patent
Zhang et al.

(10) Patent No.: US 11,200,711 B2
(45) Date of Patent: Dec. 14, 2021

(54) SMART FILTERING FOR PET IMAGING INCLUDING AUTOMATIC SELECTION OF FILTER PARAMETERS BASED ON PATIENT, IMAGING DEVICE, AND/OR MEDICAL CONTEXT INFORMATION

(71) Applicant: KONINKLIJKE PHILIPS N.V., Eindhoven (NL)

(72) Inventors: Bin Zhang, Cleveland, OH (US); Zhiqiang Hu, Twinsburg, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 407 days.

(21) Appl. No.: 15/770,783

(22) PCT Filed: Nov. 16, 2016

(86) PCT No.: PCT/EP2016/077804
§ 371 (c)(1),
(2) Date: Apr. 25, 2018

(87) PCT Pub. No.: WO2017/085092
PCT Pub. Date: May 26, 2017

(65) Prior Publication Data
US 2018/0315225 A1    Nov. 1, 2018

Related U.S. Application Data

(60) Provisional application No. 62/256,160, filed on Nov. 17, 2015.

(51) Int. Cl.
*G06T 11/00* (2006.01)
*G06T 5/00* (2006.01)
(Continued)

(52) U.S. Cl.
CPC ............ *G06T 11/008* (2013.01); *A61B 6/037* (2013.01); *A61B 6/5258* (2013.01);
(Continued)

(58) Field of Classification Search
None
See application file for complete search history.

(56) References Cited

U.S. PATENT DOCUMENTS 9,668,699 B2 * 6/2017 Georgescu ........... G06K 9/6255
9,730,643 B2 * 8/2017 Georgescu ............. G16H 50/30
(Continued)

FOREIGN PATENT DOCUMENTS

EP           2530490        12/2012
WO        2010/041196       4/2010

OTHER PUBLICATIONS

King, et al., "Digital Restoration of Indium-111 and Iodine-123 SPECT Images with Optiriized Metz Filters"; Journal of Nuclear Medicine, vol. 27, No. 8, Aug. 1, 1986.
(Continued)

*Primary Examiner* — Tahmina N Ansari

(57) ABSTRACT

The following relates to noise filtering in nuclear imaging systems. In one aspect, a fully automatic noise filtering system is provided in a nuclear imaging device. In some embodiments, a filter parameter selection engine is applied to an image environment of a medical image to calculate an image filter configuration for the medical image wherein the image environment includes values for one or more of an imaging subject of the medical image, an imaging device used to acquire the medical image, and a medical context of the medical image.

25 Claims, 5 Drawing Sheets

(51) Int. Cl.
*A61B 6/03* (2006.01)
*A61B 6/00* (2006.01)
*G01T 1/164* (2006.01)
*G01T 1/29* (2006.01)
*G06T 5/10* (2006.01)
*G06T 7/00* (2017.01)

(52) U.S. Cl.
CPC .......... *G01T 1/1642* (2013.01); *G01T 1/2985* (2013.01); *G06T 5/00* (2013.01); *G06T 5/10* (2013.01); *G06T 7/0012* (2013.01); *G06T 2207/10104* (2013.01); *G06T 2207/10108* (2013.01); *G06T 2207/20081* (2013.01); *G06T 2211/424* (2013.01)

(56) References Cited

U.S. PATENT DOCUMENTS

| | | | | |
|---|---|---|---|---|
| 10,438,379 | B2* | 10/2019 | Song | .................. G06T 11/006 |
| 2008/0091102 | A1* | 4/2008 | Maeda | .................. G06T 5/002 |
| | | | | 600/436 |
| 2009/0232375 | A1* | 9/2009 | Ye | .................. G01T 1/2985 |
| | | | | 382/131 |
| 2014/0369577 | A1* | 12/2014 | Collins | .................. G16H 30/20 |
| | | | | 382/128 |
| 2015/0286779 | A1* | 10/2015 | Bala | .................. G16H 40/63 |
| | | | | 386/283 |
| 2016/0350945 | A1* | 12/2016 | Song | .................. G06T 5/002 |
| 2017/0258412 | A1* | 9/2017 | Daerr | .................. A61B 6/06 |
| 2018/0315225 | A1* | 11/2018 | Zhang | .................. A61B 6/037 |

OTHER PUBLICATIONS

Chan, et al., "Median non-local means filtering for low SNR image denoising: Application to PET with anatomical knowledge"; Nuclear Science Symposium Conference, 2010 IEEE.

Chang et al, "Effects of injected dose, BMI and scanner type on NECR and image noise in PET imaging" in Physics in Medicine and Biology, vol. 56 (2011), pp. 5275-5285.

* cited by examiner

SMART FILTERING FOR PET IMAGING INCLUDING AUTOMATIC SELECTION OF FILTER PARAMETERS BASED ON PATIENT, IMAGING DEVICE, AND/OR MEDICAL CONTEXT INFORMATION

CROSS REFERENCE TO RELATED APPLICATIONS

This application is the U.S. National Phase application under 35 U.S.C. § 371 of International Application No. PCT/EP2016/077804, filed Nov. 16, 2016, published as WO 2017/085092 on May 26, 2017, which claims the benefit of U.S. Provisional Patent Application No. 62/256,160 filed Nov. 17, 2015. These applications are hereby incorporated by reference herein.

BACKGROUND

The following relates to noise filtering in nuclear imaging systems.

Radioemission imaging systems, for example, positron emission tomography (PET) or single-photon emission computed tomography (SPECT), preferably operate with minimal radiopharmaceutical administered to the subject in order to reduce the radiation dose received by the patient. Similarly, transmission computed tomography (CT) preferably operates at the lowest feasible x ray dosage. However, a lower radiopharmaceutical dosage or lower x-ray dosage leads to imaging data with low signal to noise ratio (SNR). Iterative reconstruction is well-suited for reconstructing imaging data with low signal-to-noise ratio. However, the iterative reconstruction process by nature amplifies noise.

To combat this noise, it is known to employ filtering of the reconstructed image. However, filtering can result in significant loss of contrast/edge features, and/or resolution. The image quality is highly sensitive to the filter parameters. Existing commercial systems enable the user to adjust the filter parameters, e.g. increasing or decreasing the Gaussian smoothing parameter or so forth. However, filter parameter adjustments require familiarity with the effects of these filter parameters. Thus, unless an operator is familiar with specific filter parameters, difficulties arise in operation of known commercial systems.

SUMMARY

In one aspect, an image processing device includes an electronic device. The electronic device is programmed to: apply a filter parameter selection engine to an image environment of a medical image to calculate an image filter configuration for the medical image wherein the image environment includes values for one or more of an imaging subject of the medical image, an imaging device used to acquire the medical image, and a medical context of the medical image; apply an image filter with the image filter configuration to filter the medical image to generate a filtered medical image; and display the filtered medical image on a display component.

In another aspect, a nuclear imaging device includes a radioemission imaging system configured to acquire a medical image, and an electronic device. The electronic device is programmed to: apply a filter parameter selection engine to an image environment of a medical image to calculate an image filter configuration for the medical image; and apply an image filter with the image filter configuration to filter the medical image to generate a filtered medical image. The nuclear imaging device further includes a display component configured to display the filtered medical image.

One advantage resides in providing a low sensitivity configured PET system having a low cost of manufacturing, which achieves comparable image quality as a higher sensitivity configured PET system.

Another advantage resides in facilitating low dose PET imaging (e.g. 2~3 mCi) to achieve a lower cost-per-scan and a better patient satisfaction that would otherwise not be possible.

Another advantage resides in a PET system which performs high resolution PET imaging for superior detectability that would be otherwise not possible.

Another advantage resides in a regular sensitivity configured PET system which performs high resolution PET imaging with low dose scans providing benefits from both low cost and high resolution imaging.

Other advantages will become apparent to one of ordinary skill in the art upon reading and understanding this disclosure. It is to be understood that a specific embodiment may attain, none, one, two, more, or all of these advantages.

The invention may take form in various components and arrangements of components, and in various steps and arrangements of steps. The drawings are only for purposes of illustrating the preferred embodiments and are not to be construed as limiting the invention.

FIG. 1 diagrammatically shows a nuclear imaging system including image filtering.

DETAILED DESCRIPTION

Figure 1:
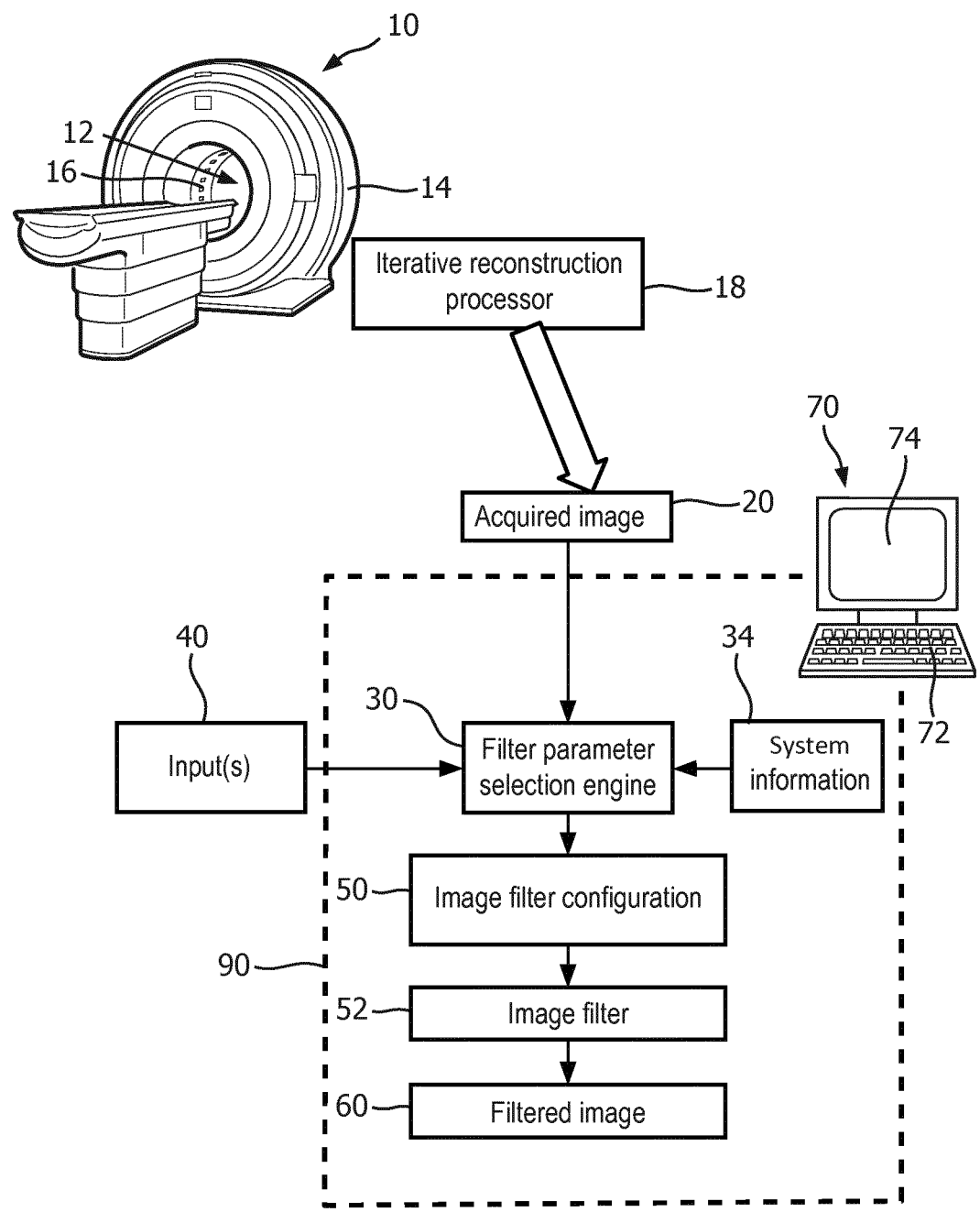

Digital positron emission tomography (PET) scanners allow for significant dose reduction (e.g. 80% reduction), low cost, safer imaging, and ultra-high resolution. However, low dose and ultra-high resolution imaging can lead to high levels of noise. Iterative PET reconstruction is commonly used in reconstructing the image, but iterative reconstruction by nature is a process that amplifies noise, and low dose image acquisitions provide noisy data that are a bad starting point for the reconstruction to work with. In addition, to achieve high resolution, smaller voxel sizes and/or a larger number of reconstruction iterations are required, which makes the noise issue even worse.

Existing techniques to combat this such as common smoothing filters, edge preserving filtering, and regularized reconstruction algorithms can suppress some noise. For example, filtering technologies such as Gaussian filtering and Median filtering can reduce noise in the image but with significant cost of resolution loss. More advanced reconstruction algorithms, such as Regularized MAP reconstruction algorithms, may serve the need for reducing noise while preserving resolution. However, these algorithms suffer from high computational cost which may make them unfeasible for busy clinical use. Other advanced filtering technologies, such as diffusion filtering and wiener filtering, may also serve the need of reducing noise and preserving resolution with low computation cost; however, they are too rigid to be applicable to all clinical scenarios with wide range of scanner configuration and properties.

In general, the use of image filtering to reduce the impact of noise requires a careful selection of filter parameters to balance the positive effects of smoothing out noise against the potential negative effects of loss of contrast or resolution. With proper selection of filter parameters, significant image improvement can be achieved; but, if the filtering is performed with non-optimal parameters then the image filtering can actually degrade the image quality. This is particularly the case with filter types such as diffusion filters or Wiener filters, for which small changes in filter settings result in large a change in image quality.

Typically, the user can configure the noise-suppressing image filter by choosing the filter parameter settings. However, effective filter configuration requires the user to understand the underlying mathematical filtering process, and in particular of the effects of different filter parameter settings on the filtering process. In a clinical setting, the radiological technician may not have a deep understanding of the mathematical processes underlying the image filtering. Even if the technician does have the requisite understanding, time constraints usually make optimal configuration of the filter impractical. The technician who does not understand the impact of the various filter parameters is likely to simply select the default filter configuration, which may be non-optimal for any particular radiological examination. At best, an experienced technician may have sufficient experience to select generally suitable filter parameter settings for certain radiology examination tasks based on the technician's past experience. Moreover, the technician is likely to use image filters with which he or she is most familiar, and may avoid using less familiar image filters provided by the system which might provide better results.

Disclosed herein is improved filtering technology which can control noise while achieving the resolution for specific clinical needs with a low computational cost. The approach provides automatic filter configuration based on the imaging environment. Information used in automatically configuring the filter can include patient data (e.g. weight, height or girth), imaging task characteristics (e.g. reason for examination, anatomical region), and imaging data acquisition system configuration (e.g. geometry, sensitivity profile, resolution). The filter configuration engine (i.e. filter parameter selection engine) may be empirically trained on a training set of filtered images constructed by filtering training images identified as to image environment with different filter settings. Each training filtered image is labeled as to image quality, and a filter parameter selection task is trained using machine learning to select filter settings yielding the highest image quality for the set of training images. Thereafter, the machine learned filter parameter selection task is applied in an inference phase to select the optimal filter settings given an input image identified as to image environment. In an alternative embodiment, a skilled radiologist manually constructs filter parameter selection rules for selecting optimal filter parameter settings (i.e. filter configuration) for a given image environment.

Because the systems and methods described herein result in a lower computational cost (e.g. a reduced burden on processor(s) and/or memory of a system), the systems and methods described herein result in improved technical functioning as compared to known systems. Although the systems and methods described herein are discussed in the context of PET scanners, the systems and methods described herein are not limited to this context and also apply in other contexts such as single-photon emission computerized tomography (SPECT) and computed tomography (CT).

FIG. 1 diagrammatically shows an example of a high level view of a nuclear imaging system using filtering. With reference thereto, a nuclear imaging machine 10, and computer 70 are shown. Nuclear imaging machine 10 is an illustrative positron emission tomography (PET) scanner that includes a housing 14 containing or supporting a radiation detector 16 in the form of one or more radiation detector rings. The radiation detector ring 16 encircles an examination region 12 into which an imaging subject (e.g., a medical patient injected with a positron-emitting radiopharmaceutical) is loaded for imaging. It will be appreciated that the dose of the radiopharmaceutical administered to the subject is preferably as low as practicable in order to minimize radiation exposure of the subject; accordingly, the signal strength is low and the signal-to-noise ratio (SNR) is high.

In FIG. 1, nuclear imaging device 10 acquires nuclear imaging data which are reconstructed by a reconstruction processor, such as an illustrative iterative reconstruction processor 18 (which may be implemented as suitable programming of the illustrative computer 70, or may be implemented by a suitably programmed dedicated PET imaging controller, not shown, or may be implemented on some other electronic data processing device), to produce an acquired image 20. In a typical approach, oppositely directed 511 keV gamma rays emitted by a positron-electron annihilation event are detected by detectors of the detector ring 16, and define a line of response (LOR). The gamma rays of each LOR can be thought of as a "forward projection" to the detectors. In one approach, the iterative reconstruction processor 18 reconstructs the image by assuming an initial radiopharmaceutical distribution, computing a forward projection data set for that distribution, comparing this computed distribution with the measured distribution of LORs, and adjusting the radiopharmaceutical distribution in an iterative fashion until the computed forward projection substantially matches the measured LOR data set. The final radiopharmaceutical distribution is then the reconstructed image. In practice, the iterative reconstruction can incorporate various known improvements such as employing an attenuation map to account for attenuation or scatter of 511 keV gamma rays by the subject. In a variant known as time-of-flight (TOF) PET, the positron is localized along the LOR based on differential arrival times of the emitted oppositely directed 511 keV gamma rays. In other embodiments, another imaging modality may be used, such as single-photon emission computed tomography (SPECT). In the SPECT technique, single gamma rays are detected along a line (or plane) defined by a collimator, and an analogous iterative reconstruction technique is employed.

The reconstructed image 20 is sent to an image filter system 90 implemented on the computer 70. Alternatively, the image filter system 90 may be implemented on a PET imaging controller (not shown) or other electronic data processing device. The image filter system 90 may be implemented on the same electronic device as the filter system 90 or (if the image filtering is performed post-reconstruction) on a different device. A filter parameter selection engine 30 of the image filter system 90 performs filter configuration based on an image environment that includes values for one or more of (1) an imaging subject of the medical image 20, (2) the imaging device 10, 18 used to acquire the medical image 20, and/or (3) a medical context. Values of the image environment may be received as medical image system information 34. This information may be available as metadata associated with the image 20, as such metadata may be annotated to the image 20 by the imaging system 10, 18 or by a Picture Archiving and Communication System (PACS) which stores the image 20. Information such as imaging system configuration, sensitivity, and resolution are commonly annotated to the image 20 as part of the DICOM header. Additionally or alternatively, values of the image environment of the image 20 may be provided as inputs 40 provided by a user via a user interface device such as an illustrative computer keyboard 72. In some embodiments, values may be obtained from other sources such as an Electronic Medical (or Health) Record (EMR or EHR). An image filter configuration 50 is selected by the filter parameter selection engine 30. In the illustrative embodiment, this selection is performed using a machine-learned filter parameter task E→K (where E is a vector representing the image environment 34, 40 and K is a vector representing the calculated image filter configuration 50, see FIG. 2). Alternatively, the selection of the image filter configuration based on the image environment can be performed using a look-up table manually generated by a skilled radiologist who chooses appropriate filter configurations for different types of image environments. An image filter 52 configured with the filter parameter settings 50 is applied to the acquired image 20 to filter the acquired image 20 to generate a filtered image 60. A display device, such as the computer display component 74, may display a filtered image 60, or the filtered image 60 may be used for an additional or other purpose such as computing standardized uptake values (SUV) from PET images.

In illustrative FIG. 1, the image filter system 90 is applied post-reconstruction. That is, the reconstructed image 20 is generated by the reconstruction processor 18, and then the image filter system 90 is applied to filter the reconstructed image 20. However, in embodiments in which the reconstruction processor 18 and the image filter system 90 are implemented on a common electronic device (e.g. on the imaging scanner controller), the image filter system 90 can be applied to an intermediate image generated between iterations of the iterative image reconstruction process.

The systems and methods described herein utilize the image environment to select an appropriate image filter configuration for the specific medical image being filtered. The image environment may include values for, e.g.: a total radiation event counts value for radioemission imaging data reconstructed to generate the medical image 20; an imaging study type for which the medical image 20 was acquired; an imaged anatomy that is imaged by the medical image 20; a body mass index (BMI) of the imaged patient; properties of the imaging device, for example, system sensitivity profile, and system resolution profile; or so forth. Additional examples of values that may make up the image environment may include a patient's weight, height, and girth.

Notably, these image environment inputs are not filter parameters. Thus, in some embodiments, filter parameters making up the filter configuration 50 are calculated by the filter parameter selection engine 30 entirely without receiving any portion of the image filter configuration 50 as filter parameter values input by a user.

Some of these inputs can be computed directly from the imaging data or obtained from metadata associated with the image or with corresponding PACS content, while other inputs (e.g. patient weight) may be entered by the technologist during the imaging session. The filter parameter selection component 30 then computes or selects filter parameter values based on these imaging environment inputs, so as to calculate the image filter configuration 50. The user is optionally still provided with the ability to directly enter filter parameter values, but the filter parameter selection component provides good results for those technologists not skilled in configuring the filter parameters, and provides a closer starting point for those technologists with such skill.

As previously noted, the filter parameter selection engine 30 may be constructed manually, e.g. by a skilled radiologist selection optimal filter configurations for different image environments. However, this approach is labor-intensive, and in practice even a skilled radiologist may have difficulty determining optimal filter configurations for various image environments.

Figure 2:
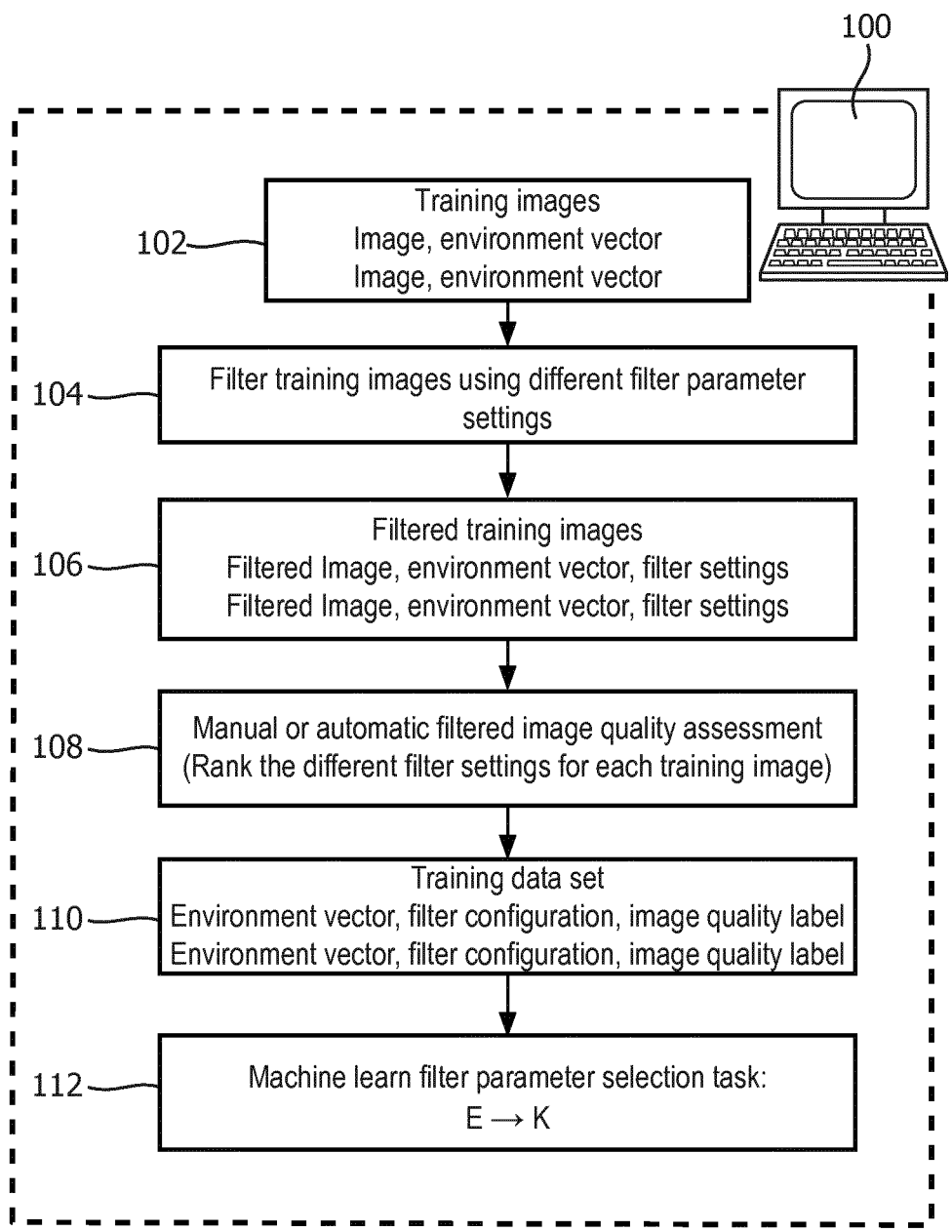
FIG. 2 shows an exemplary illustration of machine learning.

With reference to FIG. 2, in the illustrative embodiment a machine learning device 100, e.g. comprising an illustrative computer, machine learns a filter parameter selection task E→K to select the filter configuration K given the image environment E. It should be noted that the computer 100 that performs the machine learning may be different from the computer 70 of FIG. 1 that implements the "inference phase" in which the machine-learned filter parameter selection task E→K is applied to select the filter configuration to use in filtering a particular medical image 20. For example, the machine learning may be performed "off-line" using a server computer, cloud computing resource, or so forth, in which case the computer 100 is a network server, cloud computing resource, or the like. The machine learning of the filter parameter selection task E→K operates on training medical images 102, with each training medical image labeled with its image environment suitably represented as a vector (that is, a data structure of ordered values). In an operation 104, these training images are filtered by the same image filter 52 that is applied by the image filter system 90, using various different image filter configurations, in order to generate filtered training images 106. The different image filter configurations are preferably chosen to span the space of image filter configurations that are credibly expected to be used in some medical image filtering task.

In an operation 108, these filtered training images are labeled with image quality labels. This operation 108 can be performed manually for example, a team of radiologists can be assembled to visually assess and grade the filtered training images 108 with respect to image quality. Alternatively, image quality grades (i.e. labels) can be assigned using an automated process that quantitatively assesses parameters relevant to image quality such as contrast or SNR. One difficulty in this image quality assessment is that it should preferably reflect the impact of the image filter on image quality, rather than the image quality of the underlying unfiltered image. For example, if the set of training images 102 include some images that (before filtering) have good image quality and other images that (before filtering) have poor image quality, the filtered images generated from the images with poor unfiltered image quality may all rank lower than the filtered images generated from the images with good unfiltered image quality, regardless of the impact of the filtering. To reduce the impact of image quality of the unfiltered image, one approach is to consider each set of filtered images generated from a single training image with different filter configurations, and rank that set of images from poorest image quality (e.g. assigned image quality label 0%) to best image quality (e.g. assigned image quality 100%).

The output of the filtered image quality assessment operation 108 is the training data set 110. For training the filter parameter selection task E→K, the actual images (filtered or unfiltered) are not actually needed. Rather, the training set 108 includes, for each training instance, the image environment vector of the training image, the image filter settings (i.e. image filter configuration) used in the filtering, and the image quality label. The machine learning process 112 operates on these training data 110, and trains a regressor or classifier E→K such that, given as input the training image environment for that training instance, the output filter configuration closely matches the filter configuration for the filtered training image that was ranked as having highest image quality in the operation 108. The regressor or classifier may, for example, be a support vector machine, Bayesian network, genetic algorithm, or so forth. In some embodiments, the regressor or classifier E→K comprises a set of single-output regressors or classifiers, each independently trained to output the optimal setting for one image filter parameter of a set of image filter parameters making up the filter configuration. Alternatively, the regressor or classifier E→K can be a multi-output regressor or classifier that outputs a vector of optimal settings for the set of image filter parameters making up the filter configuration.

The disclosed image environment-guided smart filtering technology for low dose and/or high resolution PET imaging may be applied to a post-reconstruction image, or during the iterative image reconstruction in-between reconstruction image updates, that is, to an intermediate reconstructed image where noise control with preserved resolution is desired. The filter may be designed to suppress noise while preserving edge.

Different edge preserving filtering cores can be used in the image filter 52. For example, the Perona-Mailk diffusion filter core may be used and may be expressed as:

$$g = (\nabla I, BMI, TotCounts, StudyType, FilterStrength, etc)$$
$$g = \frac{1}{1 + (|\nabla I|/K)^2}$$

where K is the image filter configuration selected by the filter parameter selection engine 30, that is:

$$K=K(E)=K(BMI,TotCounts,StudyType,FilterStrength, etc)$$

where K (E) is an alternative notation for the machine-learned task E→K and where: |∇I| represents the local gradient factor, K ( ) represents an anisotropic weight scheme which is based on input data and system specs such as BMI, total counts (e.g. the total counts counted by detectors 16 during a PET scan), study type, user specified filtering strength and etc. Note the Perona-Mailk diffusion model is used here only as an example of possible filter core models. The filter is not limited to use this core model.

As discussed with reference to FIG. 2, the filter parameter selection engine 30 may be trained empirically using training images labeled automatically (e.g. using a contrast metric, noise metric etc.) or manually (radiologist assessment of image quality) and for which the requisite imaging environment inputs are provided. The filter may operate in image space in conjunction with iterative reconstruction (including post-iterative reconstruction filtering). For example, during an iterative image reconstruction process, the filter may be applied at each iteration.

It should be noted that in some embodiments the image filter configuration 50 may include a selection of the filter type. For example, the image filter configuration 50 may include selection of the filter type of the image filter 52 as one of (by way of non-limiting illustrative example): an anisotropic diffusion filter; a non-local mean filter; a wavelet-based non-linear filter; and a multilateral filter (e.g. a trilateral filter). It will be appreciated that such an extension is readily incorporated into the illustrative filter configuration selection task learning example of FIG. 2 by having the operation 104 filter the training images using different filter types so as to incorporate filter type into the space of image filter configuration variants spanned by the set of filtered training images 106.

Figure 3:
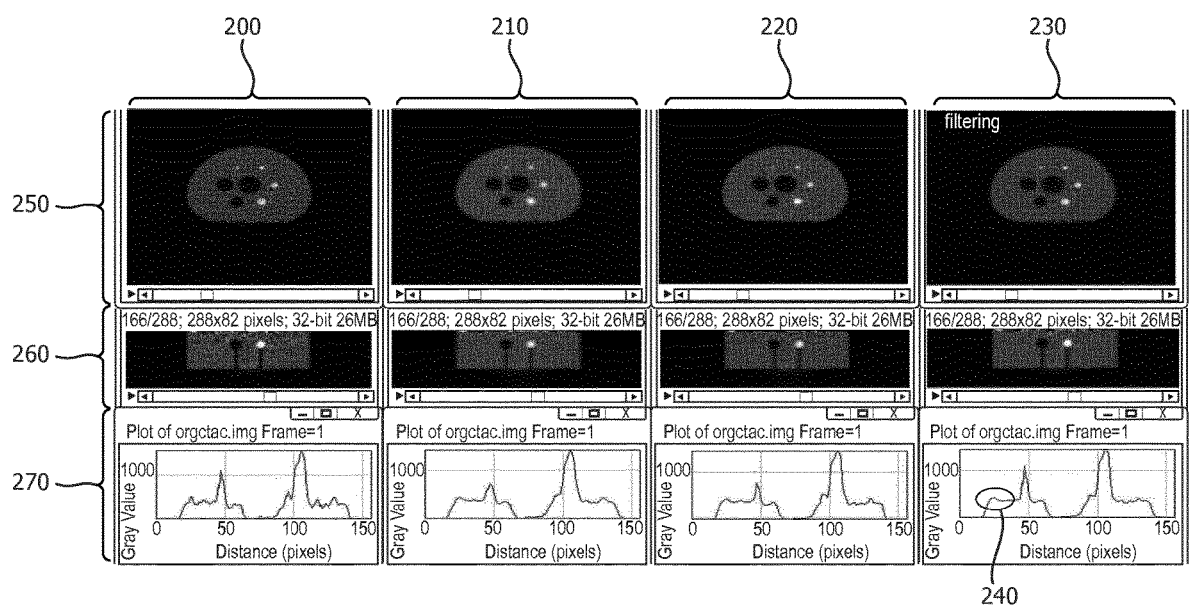
FIG. 3 illustrates examples of the impact of different filter parameter settings on image quality.

FIG. 3 illustrates examples of different types of filters that may be used, and the impact of filter configuration on the image quality of the resulting filtered image. With reference thereto, column 200 illustrates an image without any filtering. Column 210 illustrates an image with general Gaussian filtering. Column 220 illustrates an image with general Median filtering. Column 230 illustrates an image with adaptive anisotropic filtering. Row 250 shows transverse slices. Row 260 shows coronal slices. Row 270 shows profile plots crossing the centers of smallest and largest hot spheres. Graph section 240 shows that there is lower noise and minimal variation in the adaptive anisotropic tropic filtering than in the other kinds of filtering.

Figure 4:
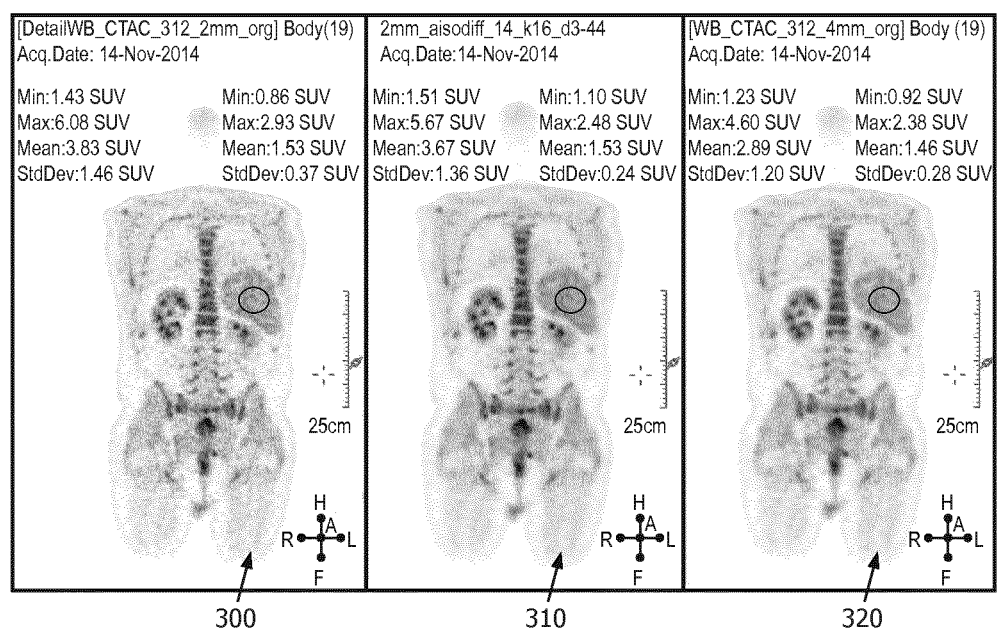
FIG. 4 illustrates further example of the impact of different filter parameter settings on image quality.

FIG. 4 illustrates an example of a comparison between patient images. With reference thereto, image 300 shows a 2 mm high resolution image without filtering. Image 310 shows a 2 mm high resolution image with adaptive filtering. Image 320 shows a 4 mm low resolution image. By applying the systems and methods described herein, the resulting 2 mm high resolution image (e.g. image 310) is achieved with similar noise levels to the 4 mm low resolution even with maintaining the 2 mm resolution. As can be seen by the examples illustrated in FIG. 4: image 300 is more noisy than the other illustrated images; image 320 is more blurry than the other illustrated images; and image 310 has the best image quality of the illustrated images.

Figure 5:
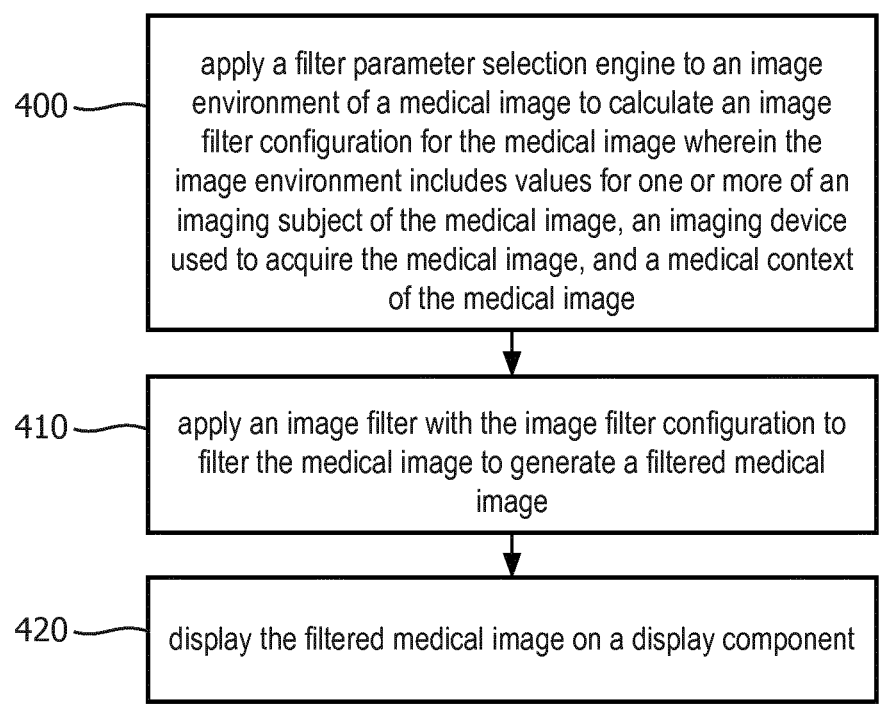
FIG. 5 illustrates an exemplary method.

FIG. 5 illustrates an example of a method described herein. With reference thereto, in step 400, a filter parameter selection engine is applied to an image environment of a medical image to calculate an image filter configuration for the medical image wherein the image environment includes values for one or more of an imaging subject of the medical image, an imaging device used to acquire the medical image, and a medical context of the medical image. In step 410, an image filter is applied with the image filter configuration to filter the medical image to generate a filtered medical image. In step 420, the filtered medical image is displayed on a display component.

It will be further appreciated that the techniques disclosed herein may be embodied by a non-transitory storage medium storing instructions readable and executable by an electronic data processing device (such as the electronic device 70 and/or the electronic device 100) to perform the disclosed techniques. Such a non-transitory storage medium may comprise a hard drive or other magnetic storage medium, an optical disk or other optical storage medium, a cloud-based storage medium such as a RAID disk array, flash memory or other non-volatile electronic storage medium, or so forth.

Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. An image processing device comprising:
an electronic device programmed to:
apply a filter parameter selection engine to an image environment of a medical image to calculate an image filter configuration for the medical image wherein the image environment includes values for one or more of a patient of the medical image, an imaging device used to acquire the medical image, and a medical context of the medical image;
apply an image filter with the image filter configuration to filter the medical image to generate a filtered medical image; and
display the filtered medical image on a display component;
wherein the image environment of the medical image includes parameters selected from a group consisting of:
a body mass index (BMI);
an imaged anatomy that is imaged by the medical image;
an imaging study type; and
a resolution of an imaging system used to acquire the medical image.

2. The image processing device of claim 1 wherein:
the filter parameter selection engine applies a machine-learned filter parameter task E→K where E is a vector representing the image environment and K is a vector representing the calculated image filter configuration; and
the image filter applies a filter function g(I,K) where I denotes the medical image.

3. The image processing device according to claim 1, wherein the image environment of the medical image includes parameters selected from a group consisting of:
an imaged anatomy that is imaged by the medical image;
an imaging study type; and
a resolution of an imaging system used to acquire the medical image.

4. The image processing device according to claim 1, wherein the image filter configuration includes a filter type selected from the group consisting of:
an anisotropic diffusion filter;
a non-local mean filter;
a wavelet-based non-linear filter; and
a multilateral filter.

5. The image processing device according to claim 1, wherein the electronic device does not receive any portion of the image filter configuration as filter parameter values input by a user.

6. The image processing device according to claim 1, wherein the electronic device is programmed to:
receive at least one value of the image environment via a user interface device; and
determine at least one value of the image environment from metadata associated with the medical image.

7. The image processing device according to claim 1, wherein the electronic device is further programed to:
generate the medical image by performing an iterative image reconstruction process including at least two iterations on imaging data; and
wherein the operation of applying the image filter with the image filter configuration to filter the medical image includes applying the image filter on an intermediate reconstructed image generated between successive iterations of the iterative image reconstruction process.

8. The image processing device according to claim 1, wherein the electronic device is further programed to:
generate the medical image by performing an iterative image reconstruction process including at least two iterations on imaging data; and
wherein the operation of applying the image filter with the image filter configuration to filter the medical image is performed after completion of the iterative image reconstruction process.

9. The image processing device according to claim 1, further comprising:
a machine learning device comprising an electronic processing device programmed to learn a machine learning task E→K where E is a vector representing the image environment and K is a vector representing the calculated image filter configuration.

10. The image processing device of claim 9 wherein the machine learning device learns the machine learning task E→K using training data generated by:
filtering training images using the image filter with different image filter configurations to generate filtered training images; and
generating a training instance for each filtered training image including a vector representing the environment of the training image, a vector representing the image filter configuration used in the filtering, and an image quality label for the filtered training image.

11. A nuclear imaging device comprising:
a radioemission imaging system configured to acquire a medical image;
an electronic device programmed to:
apply a filter parameter selection engine to an image environment of a medical image to calculate an image filter configuration for the medical image, the filter parameter selection engine being empirically trained using machine learning on a training set of filtered images constructed by filtering training images identified as to a given image environment; and
apply an image filter with the image filter configuration to filter the medical image to generate a filtered medical image; and
a display component configured to display the filtered medical image;
wherein the image environment of the medical image includes parameters selected from a group consisting of:
a body mass index (BMI);
an imaged anatomy that is imaged by the medical image;
an imaging study type; and
a resolution of an imaging system used to acquire the medical image.

12. The nuclear imaging device of claim 11 wherein the image environment includes values for a patient of the medical image.

13. The nuclear imaging device of claim 11 wherein the image environment includes values for an imaging device used to acquire the medical image.

14. The nuclear imaging device of claim 11 wherein the image environment includes values for a medical context of the medical image.

15. The nuclear imaging device according to claim 11, wherein the image filter configuration includes a filter type.

16. The nuclear imaging device according to claim 11, wherein the electronic device does not receive any portion of the image filter configuration as filter parameter values input by a user.

17. The nuclear imaging device according to claim 11, wherein the radioemission imaging system includes one of:
a positron emission tomography (PET) imaging system generating PET imaging data; and a single photon emission computed tomography (SPECT) imaging system generating SPECT imaging data.

18. The nuclear imaging device according to claim 17, wherein the radioemission imaging system further includes:
an image reconstruction processor comprising said electronic device programmed to generate the medical image by performing an iterative image reconstruction process including at least two iterations on the positron emission tomography (PET) or single photon emission computed tomography (SPECT) imaging data; and
wherein the operation of applying the image filter with the image filter configuration to filter the medical image includes applying the image filter on an intermediate reconstructed image generated between successive iterations of the iterative image reconstruction process.

19. The nuclear imaging device according to claim 17, wherein the radioemission imaging system further includes:
an image reconstruction processor comprising an electronic processor programmed to generate the medical image by performing an iterative image reconstruction process including at least two iterations on the positron emission tomography (PET) or single photon emission computed tomography (SPECT) imaging data; and
wherein the operation of applying the image filter with the image filter configuration to filter the medical image is performed after completion of the iterative image reconstruction process.

20. The nuclear imaging device according to claim 11, further comprising:
a machine learning device comprising an electronic processing device programmed to learn a machine learning task E→K where E is a vector representing the image environment and K is a vector representing the calculated image filter configuration.

21. An image processing method, the method performed by one or more processors, comprising:
selecting a filter type for an image environment of a reconstructed medical image wherein the image environment includes values for one or more of a patient of the medical image, an imaging device used to acquire the medical image, and a medical context of the medical image;
applying an image filter of the selected filter type to filter the reconstructed medical image to generate a filtered medical image; and
displaying the filtered medical image on a display component.

22. The image processing method according to claim 21, wherein the filter type is selected from the group consisting of: an anisotropic diffusion filter; a non-local mean filter; a wavelet-based non-linear filter;
and a multilateral filter.

23. The image processing method according to claim 21, further comprising:
generating the reconstructed medical image by performing an iterative image reconstruction process including at least two iterations on imaging data; and
wherein the operation of applying the image filter of the selected filter type to filter the reconstructed medical image includes applying the image filter of the selected filter type on an intermediate reconstructed image generated between successive iterations of the iterative image reconstruction process.

24. The image processing method according to claim 21, further comprising:
generating the reconstructed medical image by performing an iterative image reconstruction process including at least two iterations on imaging data; and
wherein the operation of applying the image filter of the selected filter type to filter the reconstructed medical image is performed after completion of the iterative image reconstruction process.

25. The image processing method according to claim 21, wherein the image environment of the medical image includes parameters selected from a group consisting of:
a body mass index (BMI);
an imaged anatomy that is imaged by the medical image;
an imaging study type; and
a resolution of an imaging system used to acquire the medical image.

\* \* \* \* \*